(12) United States Patent
Gollhofer

(10) Patent No.: US 6,302,856 B1
(45) Date of Patent: Oct. 16, 2001

(54) MEASURING DEVICE FOR DETERMINING DRAWER DISPLACEMENT

(76) Inventor: Albert Gollhofer, Oberbirken 14, D-79252 Stegen (DE)

( * ) Notice: Subject to any disclaimer, the term of this patent is extended or adjusted under 35 U.S.C. 154(b) by 0 days.

(21) Appl. No.: 09/341,773

(22) PCT Filed: Jan. 15, 1998

(86) PCT No.: PCT/EP98/00207

§ 371 Date: Aug. 19, 1999

§ 102(e) Date: Aug. 19, 1999

(87) PCT Pub. No.: WO98/31274

PCT Pub. Date: Jul. 23, 1998

(30) Foreign Application Priority Data

Jan. 21, 1997 (DE) .............................................. 197 01 838

(51) Int. Cl.[7] .................................................. A61B 5/00
(52) U.S. Cl. ............................................................ 600/595
(58) Field of Search .................................... 600/587, 592, 600/595

(56) References Cited

U.S. PATENT DOCUMENTS 3,782,188 * 1/1974 Korber et al. ..................... 600/595
4,804,000 * 2/1989 Lamb et al. .
5,425,775 * 6/1995 Kovacevic et al. ................. 600/587
5,454,838 * 10/1995 Vallana et al. ..................... 600/587

FOREIGN PATENT DOCUMENTS

0074407 * 8/1983 (EP) .
0710466 * 8/1996 (EP) .
WO 87/05789 * 10/1987 (WO) .

* cited by examiner

*Primary Examiner*—Max Hindenburg
(74) *Attorney, Agent, or Firm*—Pendorf & Cutliff

(57) ABSTRACT

The invention relates to a measuring device for determining drawer displacement of the tibia (44) in relation to the femur (42) on the leg (26) of a person to be examined. Said device comprises a reference frame (10) which can be attached to the calf (24) of the leg (26), two distance sensors (12, 14) which are fixedly mounted at a distance from each other on the reference frame (10) and in the proximal area of the tibia and the distal area of the femur can be moved towards the front side of the leg (26), and an analysis device (16) able to receive the output signals of the distance sensors (12, 14). The drawer displacement is thus determined, as the difference between the two isochronously captured output signals emitted by the distance sensors (12, 14), substantially irrespective of overlapping relative displacements between the calf and the reference frame (10).

16 Claims, 3 Drawing Sheets

MEASURING DEVICE FOR DETERMINING DRAWER DISPLACEMENT

BACKGROUND OF THE INVENTION

Field of the Invention

The invention concerns a measuring device for determining the drawer displacement of the tibia with respect to the femur in the leg of a patient.

In the articulating or bracing structure of the knee joint the tibia can, in a so-called drawers movement, be slid toward the front or the back in a drawers-like manner with respect to the femur, wherein the femur condyles can perform a sliding movement upon the facing tibia plateau. Such sliding or translational movements occur, besides during a simple rolling motion, also in the active extension/flexion of the knee joint and again mirror the ligamentary condition thereof. For clinical research of the drawers phenomenon the so-called "Lachmann-Test" is known, in which a researcher grasps the thigh and the calf close to the knee of a patient lying on his back and pulls the shinbone towards the front in the sense of a ventral drawer under application of pressure. This test is subjective and provides no quantitative result with respect to the displacement of a drawer. It is particularly not suited for systematic research of the relationship between the drawer freedom and the condition of the ligamentary complex.

SUMMARY OF THE INVENTION

Beginning therewith, it is an object of the invention to make possible the objective measurement of the drawer displacement at the knee joint and in particular also in functional situations, such as during standing, walking and running.

The invention is based upon the idea, of determining both the spatial position or orientation of the femur as well as also the tibia in the knee joint area by the isolated measurements in a common reference system. In order to make this possible, in accordance with the invention an attachable reference frame is provided on the calf of a leg, two distance sensors which are fixedly mounted on the reference frame spaced apart from each other and which can be moved towards the front side of the leg in the area of the proximal tibia and the distal femur, and a measurement device able to receive input signals from the distance sensors for determining the drawer displacement. Therewith it becomes possible to obtain objective, precise measured values of movements generated passively from outside as well also active drawer displacements, without it being necessary to immobilize the leg. Further, considering the parallel determination of the starting signal by both distance sensors, it becomes unnecessary that the reference framework be completely rigidly fixed or connected with the calf, which during an active drawer displacement test in particular is not satisfactorily possible.

It is advantageous when a distance sensor is directed against the front kneecap surface (Facies anterior patellae) as outer or external reference surface for the position of the femur medial condyles and the other distance sensor is directed against the front shinbone tuberosity (Tuberositas tibiae) as reference point for the position of the tibia head.

In order to place the starting signals of the distance sensors in direct perspective or context to the transverse displacement to be measured, the distance sensors are provided with parallel measuring extensions, which run parallel to the tibia plateau in the essentially anterior-posterior direction. Therewith the drawer displacement can be determined in simple manner according to measurement of a differential value of the starting signals of the distance sensors.

For adjustment to a suitable measuring position the distance sensors are preferably limitedly movable in all three spatial directions and are fixable in their displacement direction in fixed position on the reference framework.

The distance sensors can comprise a capacitative, inductive or ohmic resistance based odometer sensor, of which the measurement distance is predetermined with respect to a reference point fixed with respect to the frame. Therewith it becomes possible to determine the instantaneous respective spatial positions of the sensed leg surfaces in a common reference system formed by the reference framework. In a simplified embodiment the distance sensors are formed as linear potentiometers, of which the two free ends of the sliders can be urged against the front side of the leg against a spring bias.

Alternatively the distance sensors can be formed as ultrasonic, infrared or laser sensors for contactless measurement.

It is advantageous when the reference framework is supportable against the front side of the calf via a support padding. The support padding makes possible a substantially painless fitting to the anatomy, wherein foam materials such as polystyrene or polyurethane in particular exhibit satisfactory characteristics. The reference signal is constructed appropriately in a lightweight manner, in order to be carried on the calf, wherein it can be fixed to the calf by means of circular tensionable VELCRO closure straps. In this manner it becomes possible in an advantageous manner to form a secure attachment of the reference framework to the calf, so that relative movements of the reference framework can substantially be avoided.

It is advantageous when external forces can be introduced into the calf via a force transmission device preferably including a band sling, wherein the amount of the force to be imparted can be determined by a force recorder.

In a mobile embodiment it is advantageous, when the measurement device includes a hand-held portable indicator unit, by means of which the sensed values of the distance sensors can be displayed in an LCD-display. Therein it can be sufficient, when the maximal values obtained during a measurement cycle are indicated. For wireless connection of the distance sensors with the evaluation device a telemetric device can be provided.

It is further advantageous, when the evaluation device includes a microcomputer which, via an analog/digital converter, is in communication with the digitalized output signals of the distance sensors and in certain cases the output signals of a force recorder. Thereby the data processing can be carried out in suitable manner for purposes of scientific evaluation.

For supplemental research of muscular activation electromyographic signals can be detected by external electrodes, wherein in particular the M. biceps femoris in the thigh area and the M. gastrocnemius in the calf are suitable as sensory points.

In order to make it possible to detect possibly the rotational movement of the reference framework with respect to the calf, there are preferably provided at least three distance sensors on the reference framework, wherein a first distance sensor is provided in the proximal tibia area and a second distance sensor in the distal femur area against the front side of the leg, and wherein at least a further distance sensor is directed against the calf in a horizontal and/or vertical separation from the second distance sensor.

BRIEF DESCRIPTION OF THE DRAWINGS

In the following the invention will be described in greater detail by reference to the embodiment represented in schematic manner in the drawings. There is shown FIGS. 1 and 2 a measurement device for determining the drawer displacement fixed to a leg in lateral and frontal view.

DETAILED DESCRIPTION OF THE INVENTION

The measurement device represented in the figure is comprised essentially of a reference framework 10, two distance sensors 12, 14 fixed to the framework in fixed separation from each other as well as a processing device 16 for receiving the output signals of the distance sensors 12, 14 for determining the drawer displacement.

Figure 1:
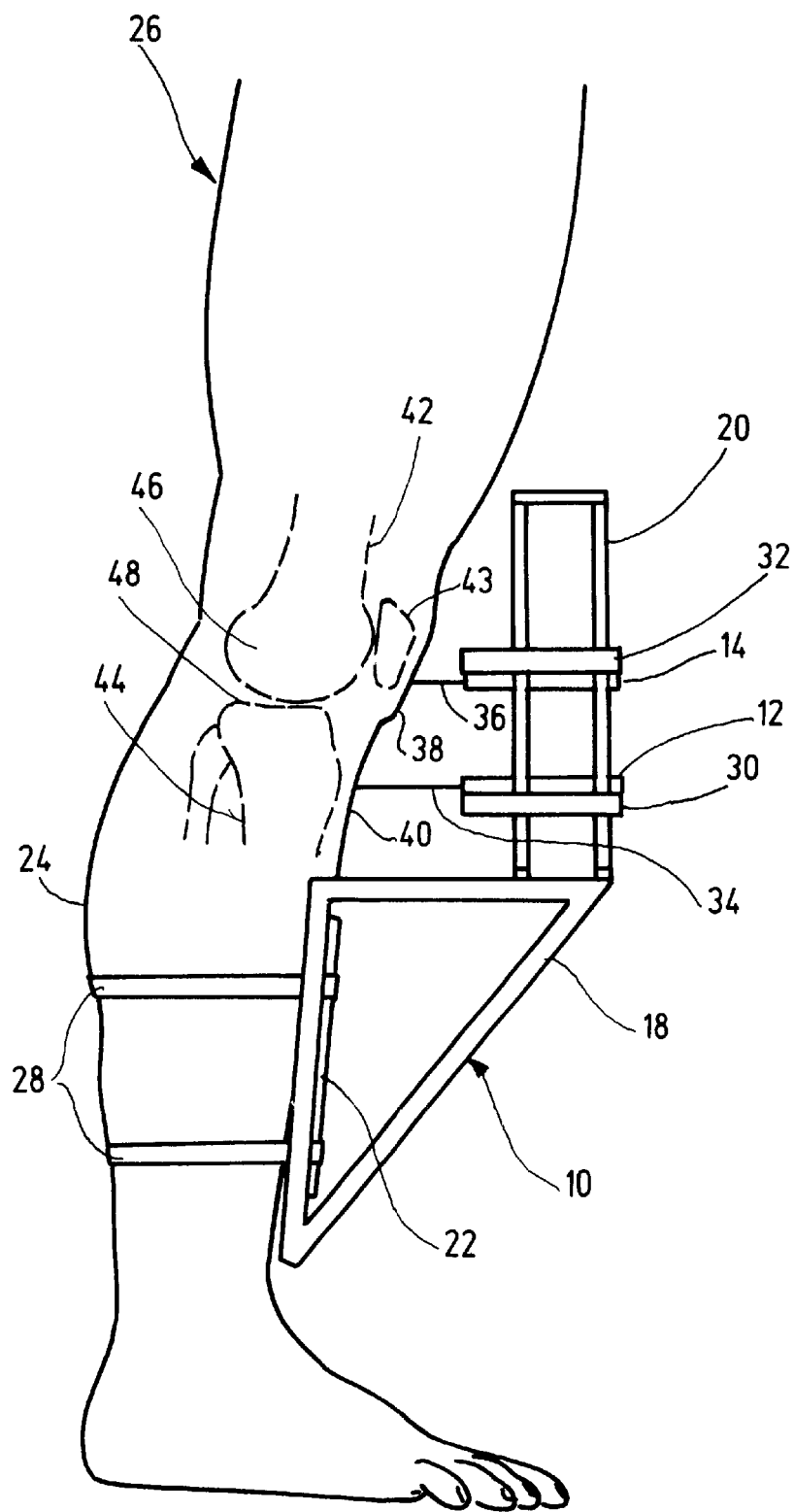
Figure 2:
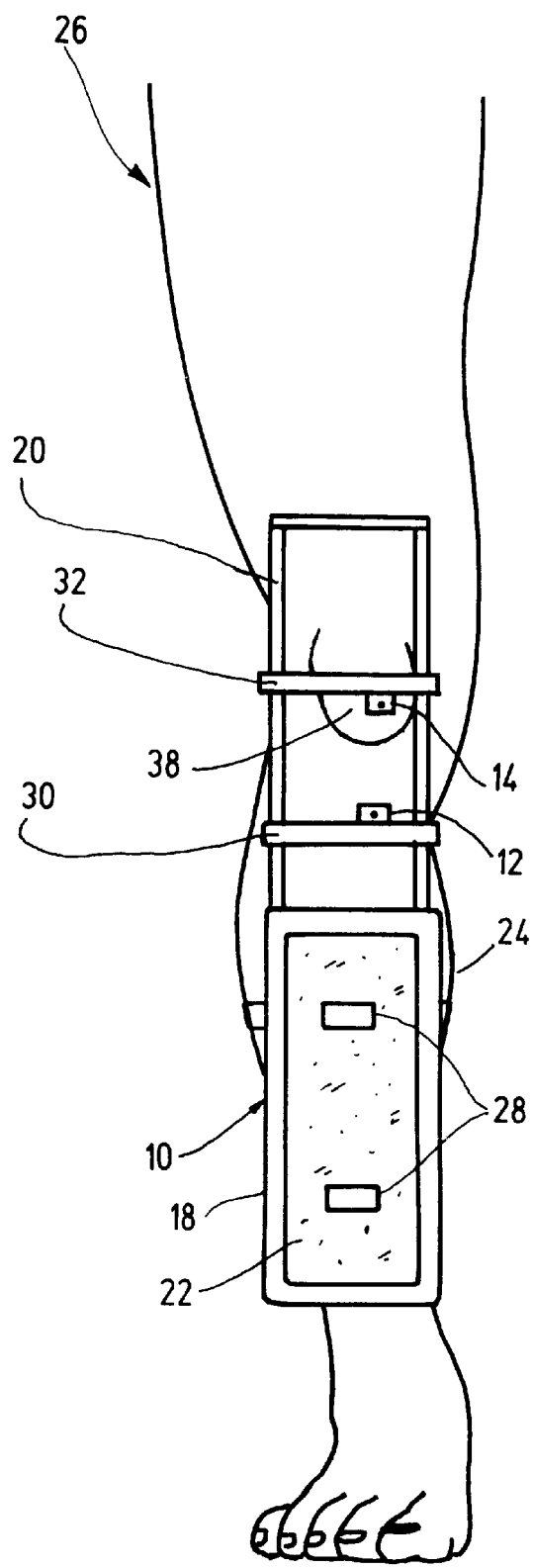

As shown in FIGS. 1 and 2, the reference framework 10 exhibits a scaffold-like construction, wherein the lower carrier construction 18 forms a platform for a support assembly 20. The carrier construction 18 is supportable on a front side of the calf 24 of a leg 26 via a support cushion 22 of polystyrene and is attached by means of VELCRO straps 28. In order to prevent a rotation about the calf axis, supplemental support struts can be provided, which engage laterally and medially in the area of the shinbone.

On the support assembly 20 two mounting plates 30, 32 oriented in a transverse plane are provided vertically displaceable, upon which the distance sensors 12, 14 are horizontally displaceable and lockable in an adjusted displacement position.

The distance sensors 12, 14 are formed as linear potentiometers, of which the sliders are slideable via sensing rods 34, 36 against a frame-fixed linear resistor, wherein the sensing rods 34, 36 are spring biased in the direction of their free end. For measurement of drawer movement, the linear potentiometers 12, 14 are so oriented in their position with respect to the knee joint, that the upper sensor rod 36 is pressed against the front kneecap surface 38 and the lower sensor rod is pressed against the front shinbone tuberosity 40. These outer leg regions serve as reference points for the distal section of the femur 42 or, the as the case may be, the proximal section of the tibia 44 (FIG. 1). In a backwards or forwards drawer displacement the femur condyles 46 slide upon the tibia plateau 48 with respective relative displacement in the anterior-posterior direction. Accordingly, the sensing rods 34, 36 are so positionally associated so that the displacement paths of the femur 42 and the tibia 44 are directly measurable with respect to the reference frame 10.

Figure 3:
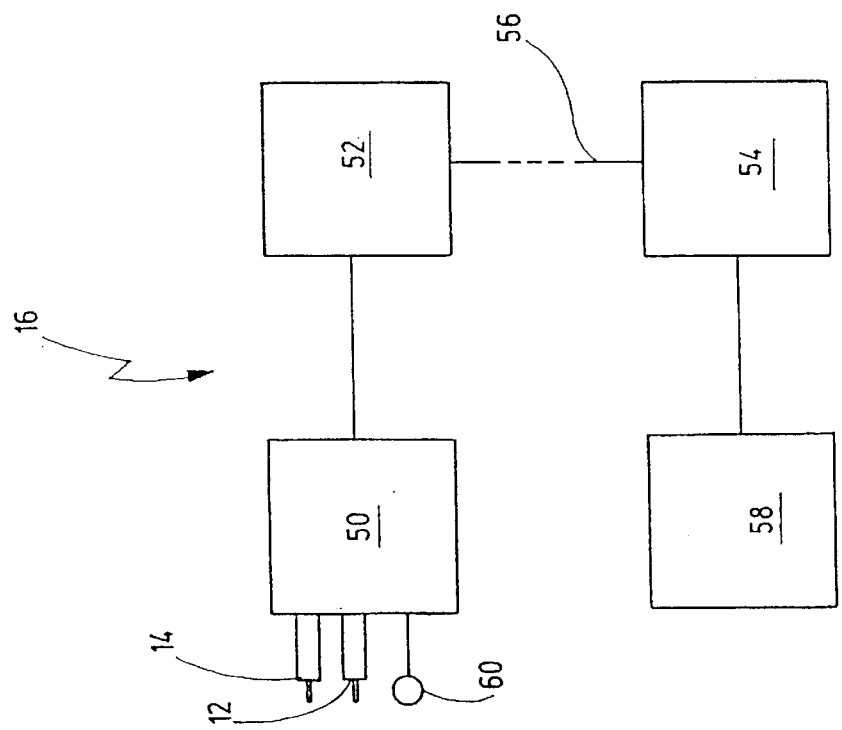
FIG. 3 a block diagram of elements for data detection and processing of the measuring device.

It is fundamentally of advantage when a rigid as possible fixation of the reference frame 10 is made to the calf 24. In order to detect still possible rotational movements of the reference frame 10 with respect to the calf 24, at least a further distance sensor 15 is provided. When this, as shown in FIG. 3, is positioned or oriented along the longitudinal axis of the tibia 44 in vertical separation from the distance sensor 12, then a possible rotation or as the case may be tilting movement along the sagittal plain can be detected. When a further distance sensor (not shown) is provided at the same height as the tibia 44 in horizontal separation next to the distance sensor 12, then also a rotation of the reference frame 10 about the axis of the tibia 44 can be detected.

As can be seen from FIG. 3, the output signals of the potentiometers 12, 14 are amplified in a signal processing unit 50 and in certain cases digitalized as well as indicated on an LCD-display, wherein the unit 50 is preferably provided on the body of the subject. The data can be transmitted via a transmitter module 52 and a receiver module 54 of a telemetric device over a radio pathway 56 to a stationary processing unit 58. In a laboratory situation the signal processing unit 50 can be directly connected to a data processing unit 58 in the form of a personal computer, wherein the digitalization of the data is accomplished by an analog-digital converter in the form of a plug-in card in the personal computer.

Passive drawer movements can be observed under the influence of external forces. In order to produce reproducible measuring conditions, a force recorder 60 can be provided, by means of which the applied force can be measured and therewith the further evaluations are possible. Further, for enhancing the reproducibility of the measurements, a not shown angular measuring system can be provided for measuring bending or, as the case may be, stretching position of the knee joint.

Drawer movements are presumably triggered by mechano receptor muscle reflexes for protection of the knee joint from extreme positions. Besides the measurement of the purely mechanical displacement, it is thus also of interest to register signals of the neuromuscular system, as can be detected in the form of electromyographs by means of surface electrodes.

Figure 4:
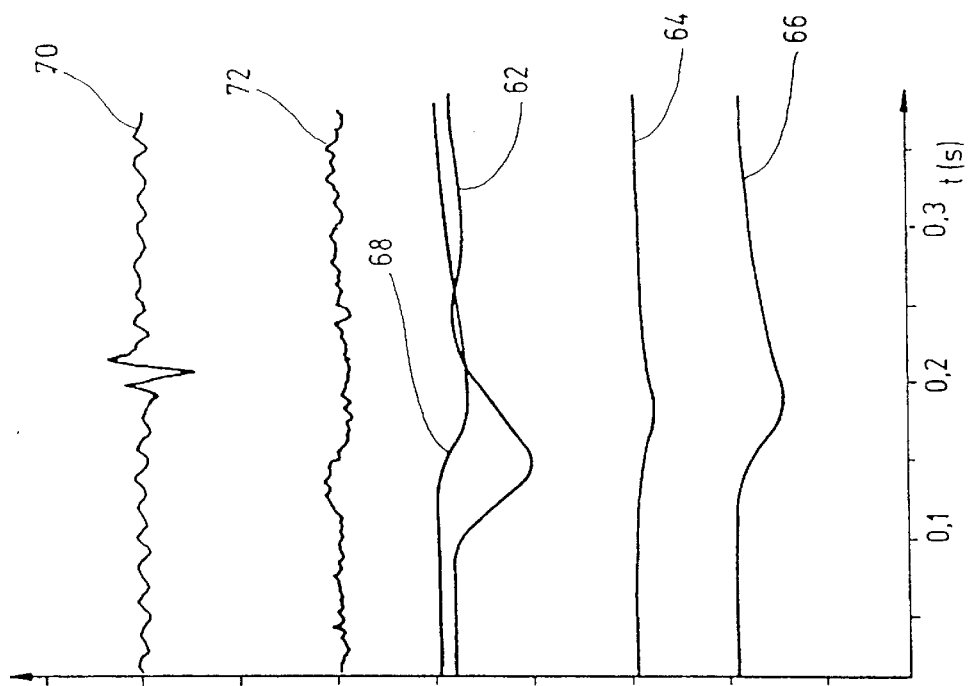
FIG. 4 a chronological diagram of various measurement signals detected by the measurement device.

In FIG. 4 time resolved recorded signal amplitudes of the various measurement sensors in arbitrary units are shown over time. The curve 62 provides the force impulse introduced into the calf 24 as measured by the force recorder 60. On the basis of the signal 64 of the linear potentiometer 12 there is to be recognized a small temporarily delayed movement of the tibia 44 with respect to the reference position 10, while the signal 66 of the potentiometer 14 shows the movement of the patella 43 and therewith the femur 46. The actual drawer displacement can finally be seen as the differential curve 68 of the signal curves 64 and 66. Besides this, in FIG. 4 there are shown also the EMG-signals of the biceps femoris (curve 70) and gastrocnemius (curve 72) detected at the same time, which show activation in connection with the force introduction.

In summary the following is to be concluded: The invention relates to a measuring device for determining drawer displacement of the tibia 44 in relation to the femur 42 on the leg 26 of a person to be examined, comprising a reference frame 10 which can be attached to the calf 24 of the leg 26, two distance sensors 12, 14 which are fixedly mounted spaced apart from each other on the reference frame 10 and can be moved towards the front side of the leg 26 in the proximal area of the tibia and the distal area of the femur, and an analysis device 16 able to receive the output signals of the distance sensors 12, 14. The drawer displacement is thus determined as the difference between the two isochronously captured output signals emitted by the distance sensors 12, 14 substantially irrespective of overlapping relative displacements between the calf and the reference frame 10.

What is claimed is:

1. Measuring device for determining drawer displacement of the tibia (44) in relation to the femur (42) on the leg (26) of a person to be examined, comprising a reference framework (10) fixable on the calf (24) of the leg (26), two independent distance sensors (12, 14) which are fixedly mounted, spaced apart from each other, on a reference framework (10) such that when said reference framework is fixed on the calf of the leg of the person to be examined, one distance sensor is in the proximal area of the tibia and one distance sensor is in the distal area of the femur, towards the front surface of the leg (26), and an analysis device (16) able to receive output signals from the distance sensors (12, 14).

2. Method for measuring the drawer displacement of the tibia (44) relative to the femur (42) in the leg (26) of a patient, said method comprising:

(a) applying to said leg a measuring device comprising a reference framework (10) fixable on the calf (24) of the leg (26), two distance sensors (12, 14) which are fixedly mounted, spaced apart from each other, on a reference framework (10) in the proximal area of the tibia and the distal area of the femur, and which can be moved towards the front surface of the leg (26) and provide output signals corresponding to their degree of extension, and an analysis device (16) able to receive output signals from the distance sensors (12, 14), (b) directing one distance sensor (14) against the Facies anterior patellae (38) as reference surface for the femur (42) and the other distance sensor (12) against the Tuberositas tibiae (40) as reference surface for the tibia (44), and (c) moving the femur condyles (46) in a drawers movement relative to the tibia plateau (48) and measuring the movement of the distance sensors relative to said frame as measurement of the displacement of the femur (42) and tibia (44).

3. A method according to claim 2, wherein the measurement paths of the distance sensors (12, 14) run parallel to the tibia plateau in an essentially anterior-posterior direction.

4. Measuring device for determining drawer displacement of the tibia (44) in relation to the femur (42) on the leg (26) of a person to be examined, comprising a reference framework (10) fixable on the calf (24) of the leg (26), two distance sensors (12, 14) which are fixedly mounted, spaced apart from each other, on a reference framework (10) in the proximal area of the tibia and the distal area of the femur, and which can be moved towards the front surface of the leg (26), and an analysis device (16) comprising a processing unit (50, 58) for receiving and processing output signals (64, 66) from said distance sensors (12, 14), wherein said processing unit (50, 58) determines the drawer displacement according to a differential curve (68) of the simultaneously registered output signals (64, 66) of the distance sensors (12, 14).

5. Measuring device according to claim 1, wherein the distance sensors (12, 14) are limitedly movable for adjustment in all three spatial directions relative to said reference framework (10) and in their displaced position are fixable on the reference framework (10).

6. Measuring device according to claim 1, wherein the distance sensors (12, 14) are selected from the group consisting of capacitative, inductive and ohmic resistance based odometer sensors, of which the measurement length is predetermined with respect to a frame-fixed reference point.

7. Measuring device according to claim 1, wherein the distance sensors are formed as linear potentiometers (12, 14), of which the sliders (36, 38) are spring biased towards their two free ends and can be urged against the front side of the leg (26).

8. Measuring device according to one of claim 1, wherein the distance sensors (12, 14) are formed as ultrasonic, infrared or laser sensors for contactless measurement.

9. Measuring device according to claim 1, wherein the reference framework (10) is supported on the front side of the calf (24) by a support cushion (22).

10. Measuring device according to claim 1, wherein the reference framework (10), which can be worn on the calf (24), is securable by circular closure straps (28) tightenable around the calf.

11. Measuring device according to claim 1, wherein a force transmission device is coupled to a force recorder (60), for introduction of force into the calf (24).

12. Measuring device according to claim 1, wherein the analysis device (16) comprises a hand-held processing unit (50), by means of which the sensed values of the distance sensors (12, 14) sensed during a measurement cycle can be represented in an LCD-display.

13. Measuring device according to claim 12, further including a transmitter and a receiver module (52, 54) for communication between the distance sensors (12, 14) and the processing unit (58) over an wireless radio path (56).

14. Measuring device according to claim 12, wherein the processing unit (50, 58) comprises a microcomputer (58), which can be acted upon by the output signals of the distance sensors (12, 14) and optionally the output signals of at least one of a force recorder and a goniometer.

15. Measuring device according to claim 1, further comprising surface electrodes for detection of electromyographic signals (70, 72).

16. Measuring device according to claim 1, wherein at least first, second and third distance sensors (12, 14, 15) are provided on the reference framework (10), of which the first distance sensor (14) is adapted to be directed against the front side of the leg (26) in the distal femur area, the second distance sensor (12) is adapted to be directed against the front side of the leg (26) in the proximal tibia area, and the third distance sensor (15) is positioned in horizontal or vertical separation from the second distance sensor (12) and is adapted to be directed against the calf (24).

* * * * *